(12) United States Patent
Burton et al.

(10) Patent No.: US 9,861,797 B2
(45) Date of Patent: Jan. 9, 2018

(54) BALLOON CATHETER AND METHOD FOR MAKING SAME

(71) Applicant: COOK MEDICAL TECHNOLOGIES LLC, Bloomington, IN (US)

(72) Inventors: David G. Burton, Bloomington, IN (US); Thomas Lysgaard, Solroed Strand (DK); Steen Aggerholm, St. Heddinge (DK); Scott E. Boatman, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 14/721,566

(22) Filed: May 26, 2015

(65) Prior Publication Data
US 2015/0250990 A1 Sep. 10, 2015

Related U.S. Application Data

(62) Division of application No. 12/508,243, filed on Jul. 23, 2009, now Pat. No. 9,067,045.
(Continued)

(51) Int. Cl.
*B29C 49/48* (2006.01)
*A61M 25/10* (2013.01)
(Continued)

(52) U.S. Cl.
CPC .... *A61M 25/1029* (2013.01); *A61M 25/1002* (2013.01); *A61M 25/1034* (2013.01);
(Continued)

(58) Field of Classification Search
None
See application file for complete search history.

(56) References Cited

U.S. PATENT DOCUMENTS 2,927,584 A 3/1960 Wallace
3,706,550 A * 12/1972 Umehara ............... B22C 9/061
419/17
(Continued)

FOREIGN PATENT DOCUMENTS

DE 198 33 501 C1 1/2000
EP 0 204 218 B1 12/1986
(Continued)

OTHER PUBLICATIONS

International Search Report; PCT/US2009/051550 (dated Nov. 2, 2009).
(Continued)

*Primary Examiner* — Monica Huson
(74) *Attorney, Agent, or Firm* — Brinks Gilson & Lione

(57) ABSTRACT

In at least one embodiment of the present invention a balloon catheter is provided. The balloon catheter comprises a shaft having a lumen formed therethrough. Connected to the shaft is an inflatable balloon. The inflatable balloon has a balloon wall defining a balloon interior surface and a balloon exterior surface that is opposite the interior surface. In fluid communication with the balloon wall is the lumen for inflating the balloon to define an inflated state and for collapsing the balloon to define a deflated state. The balloon wall is textured in the deflated state such that the balloon interior surface is spatially registered with the balloon exterior surface. The balloon in the inflated state is tensioned to have a surface roughness substantially less than a surface roughness of the balloon in the deflated state.

4 Claims, 8 Drawing Sheets

Related U.S. Application Data

(60) Provisional application No. 61/083,730, filed on Jul. 25, 2008.

(51) Int. Cl.
*A61M 29/02* (2006.01)
*B29C 33/38* (2006.01)
*B29C 33/42* (2006.01)
*A61M 25/00* (2006.01)
*B29L 31/00* (2006.01)

(52) U.S. Cl.
CPC ......... *A61M 29/02* (2013.01); *B29C 33/3842* (2013.01); *B29C 33/42* (2013.01); *B29C 49/48* (2013.01); *A61M 2025/0057* (2013.01); *A61M 2025/1004* (2013.01); *A61M 2025/1031* (2013.01); *A61M 2025/1086* (2013.01); *B29K 2995/0072* (2013.01); *B29L 2031/7543* (2013.01)

(56) References Cited

U.S. PATENT DOCUMENTS

| | | |
|---|---|---|
| 4,650,466 A | 3/1987 | Luther |
| 5,092,348 A | 3/1992 | Dubrul et al. |
| 5,102,402 A | 4/1992 | Dror et al. |
| 5,232,444 A | 8/1993 | Just et al. |
| 5,250,060 A | 10/1993 | Carbo et al. |
| 5,250,070 A | 10/1993 | Parodi |
| 5,308,356 A | 5/1994 | Blackshear, Jr. et al. |
| 5,338,295 A | 8/1994 | Cornelius et al. |
| 5,397,307 A | 3/1995 | Goodin |
| 5,423,745 A | 6/1995 | Todd et al. |
| 5,487,730 A | 1/1996 | Marcadis et al. |
| 5,693,014 A | 12/1997 | Abele et al. |
| 5,714,110 A * | 2/1998 | Wang ............... A61M 25/0045 264/529 |
| 5,738,901 A | 4/1998 | Wang et al. |
| 5,746,745 A | 5/1998 | Abele et al. |
| 5,868,708 A | 2/1999 | Hart et al. |
| 5,904,698 A | 5/1999 | Thomas et al. |
| 5,954,740 A | 9/1999 | Ravenscroft et al. |
| 6,007,545 A | 12/1999 | Venturelli |
| 6,010,480 A | 1/2000 | Abele et al. |
| 6,033,379 A | 3/2000 | Barra et al. |
| 6,110,192 A | 8/2000 | Ravenscroft et al. |
| 6,123,718 A | 9/2000 | Tu et al. |
| 6,129,706 A | 10/2000 | Janacek |
| 6,136,369 A | 10/2000 | Leitao et al. |
| 6,245,104 B1 | 6/2001 | Alt |
| 6,264,633 B1 | 7/2001 | Knorig |
| 6,306,162 B1 | 10/2001 | Patel |
| 6,368,338 B1 | 4/2002 | Kónya et al. |
| 6,458,097 B1 | 10/2002 | Boussignac |
| 6,458,138 B1 | 10/2002 | Sydney et al. |
| 6,478,807 B1 | 11/2002 | Foreman et al. |
| 6,500,145 B1 | 12/2002 | Bicakci et al. |
| 6,585,689 B1 | 7/2003 | Macoviak et al. |
| 6,626,861 B1 | 9/2003 | Hart et al. |
| 6,638,302 B1 | 10/2003 | Curcio et al. |
| 6,656,217 B1 | 12/2003 | Herzog, Jr. et al. |
| 6,736,841 B2 | 5/2004 | Musbach et al. |
| 6,786,889 B1 | 9/2004 | Musbach et al. |
| 6,805,898 B1 | 10/2004 | Wu et al. |
| 6,913,617 B1 | 7/2005 | Reiss |
| 6,918,927 B2 | 7/2005 | Bates et al. |
| 6,939,321 B2 | 9/2005 | Wang et al. |
| 6,960,188 B2 | 11/2005 | Jörgensen |
| 6,979,346 B1 | 12/2005 | Hossainy et al. |
| 6,986,899 B2 | 1/2006 | Hossainy et al. |
| 7,004,963 B2 | 2/2006 | Wang et al. |
| 7,572,270 B2 | 8/2009 | Johnson |
| 8,226,603 B2 | 7/2012 | Von Oepen et al. |
| 2002/0098307 A1 | 7/2002 | Schwartz et al. |
| 2004/0073284 A1 | 4/2004 | Bates et al. |
| 2004/0199202 A1 | 10/2004 | Dubrul et al. |
| 2004/0236369 A1 | 11/2004 | Dubrul |
| 2004/0260333 A1 | 12/2004 | Dubrul et al. |
| 2005/0124931 A1 | 6/2005 | Fulton et al. |
| 2005/0251246 A1 | 11/2005 | Dubrul et al. |
| 2005/0261585 A1 | 11/2005 | Makin et al. |
| 2006/0020243 A1 | 1/2006 | Speck et al. |
| 2006/0116749 A1 | 6/2006 | Willink et al. |
| 2006/0167407 A1 | 7/2006 | Weber et al. |
| 2007/0016278 A1 | 1/2007 | Shippy, III et al. |

FOREIGN PATENT DOCUMENTS

| | | |
|---|---|---|
| EP | 0 746 362 B1 | 12/1996 |
| EP | 0 891 201 B1 | 1/1999 |
| EP | 1 344 548 A1 | 9/2003 |
| GB | 2 046 096 A | 11/1980 |
| WO | WO 94/23787 | 10/1994 |
| WO | WO 95/05860 | 3/1995 |
| WO | WO 98/11933 | 3/1998 |
| WO | WO 03/039628 A2 | 5/2003 |

OTHER PUBLICATIONS

Communication from the European Patent Office on European Patent Application 09790771.1-1506, dated Sep. 30, 2015.
European Office Action dated Sep. 4, 2017.

* cited by examiner

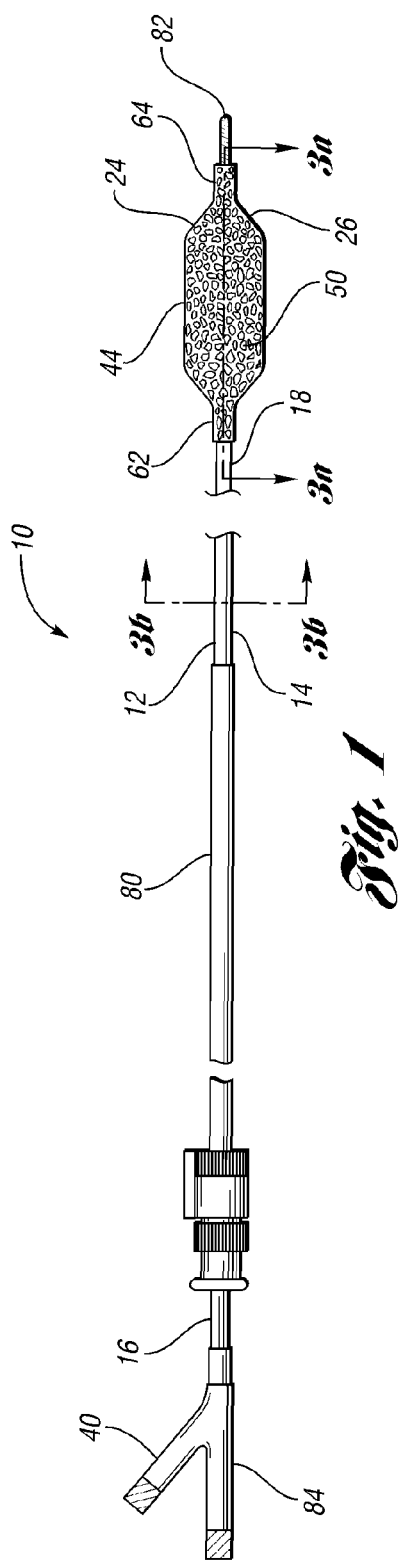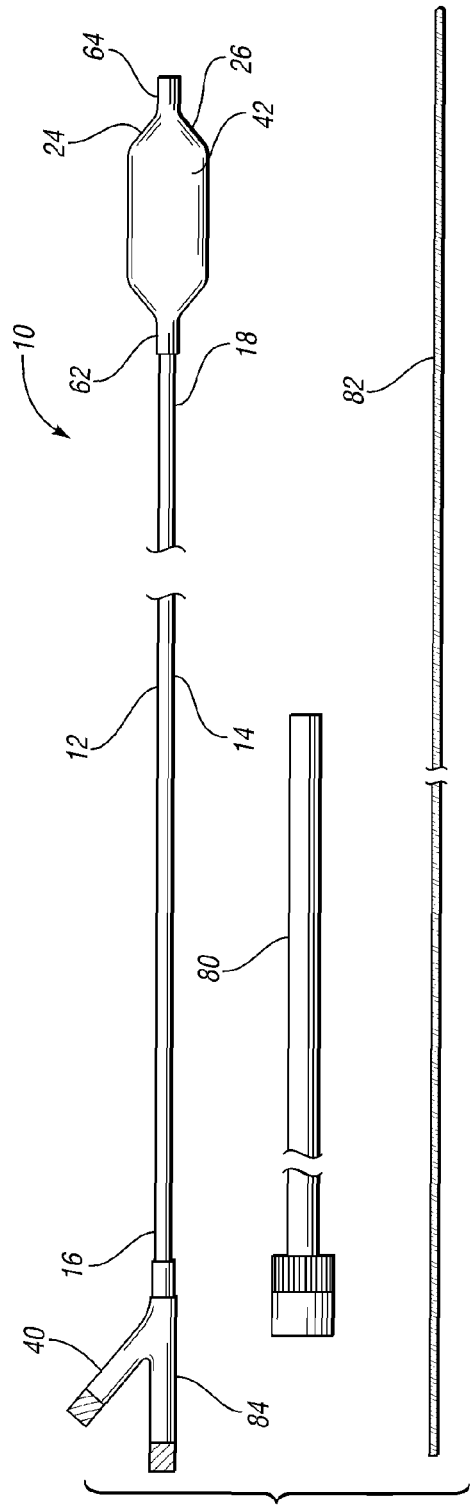

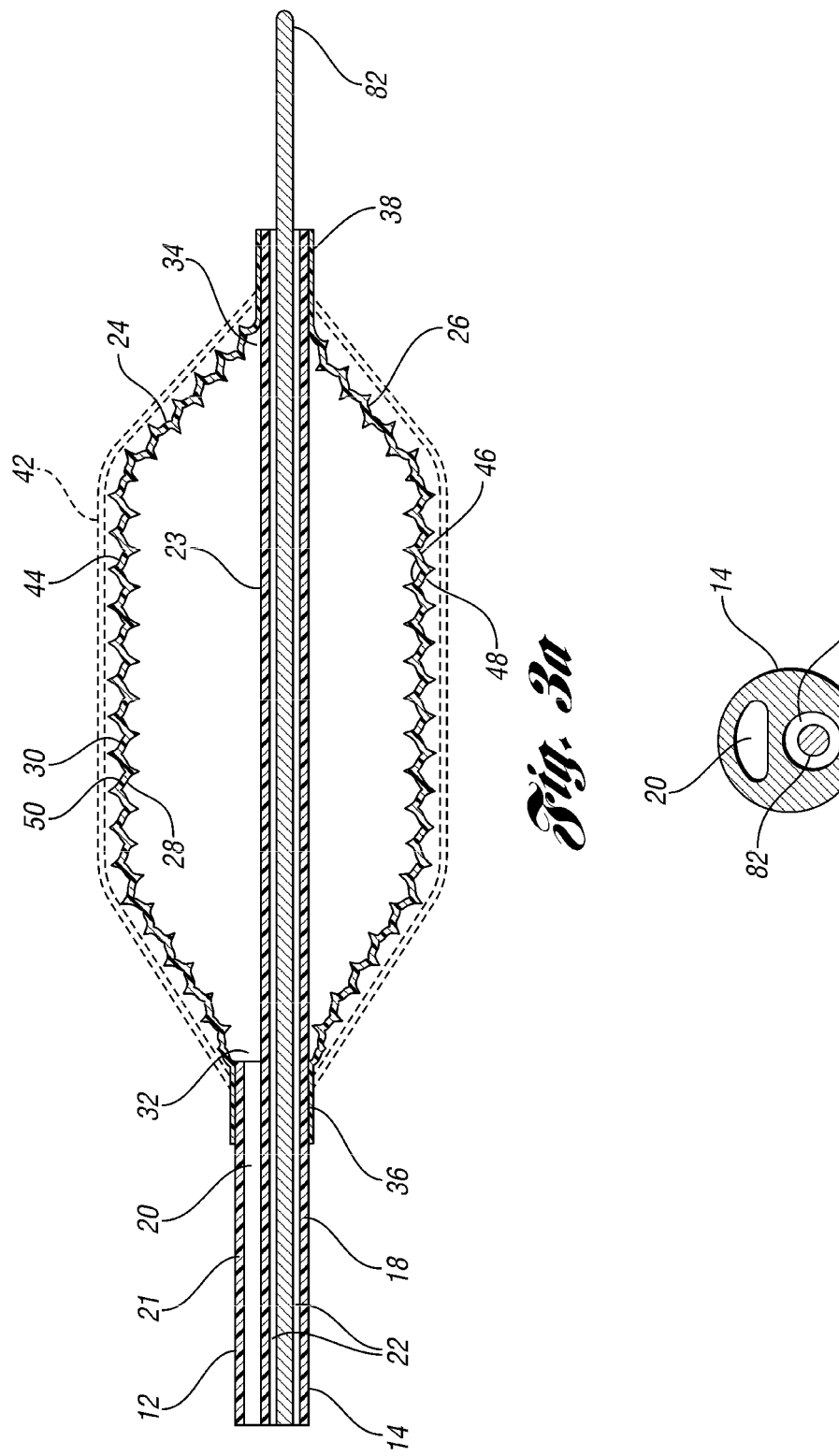

BALLOON CATHETER AND METHOD FOR MAKING SAME

CROSS-REFERENCE TO RELATED APPLICATIONS

This application is a Divisional of U.S. patent application Ser. No. 12/508,243, filed Jul. 23, 2009, and claims priority to and all available benefits of U.S. Provisional Application No. 61/083,730, filed on Jul. 25, 2008, and which is hereby incorporated by reference in their entirety.

BACKGROUND OF THE INVENTION

Field of the Invention

The present invention relates to medical catheters. More specifically, the invention relates to pushable balloon-tipped catheters and a method for making the balloon catheter.

Background

Pushable balloon-tipped catheters are used for the treatment of many conditions relating to body vessels including arteries and veins. For such treatments, a wire guide may be percutaneously inserted into the body vessel and positioned near a location where treatment is necessary. The balloon catheter may be inserted through a guide catheter over the wire guide. The distal tip of the balloon catheter is guided to the treatment location along the wire guide. Once at the treatment location, the balloon at the distal tip of the catheter is unfolded and inflated, such as for example, by pumping a mixture of saline and/or contrast solution through the catheter into the balloon. When inflated, the balloon presses against the inner wall of the body vessel to dilate the vessel. If a stent is mounted on the balloon, inflation of the balloon will also expand the stent to implant the stent within the artery. After the vessel is dilated, the balloon is deflated to collapse the balloon back onto the shaft of the catheter for retraction into the guide catheter and retrieval from the body vessel.

Sometimes difficulties may be encountered in retracting the deflating balloon back into the guide catheter. These difficulties may be attributed to various factors, such as for example, the shape of the balloon, incomplete deflation of the balloon, and/or the balloon not returning to its initial folded condition after deflation. Consequently, the force required to retract the balloon into the guide catheter may be unacceptably and/or undesirably high. Moreover, there may also be a risk that the balloon will get caught against the distal end of the guide catheter, making it difficult to remove the balloon catheter from the treatment site.

Current methods for resolving some of these difficulties have been to design balloon catheters with thinner, weaker balloon walls. Generally, a balloon having a thinner, weaker wall will present fewer difficulties on retraction from the body vessel than a balloon of the same shape having a thicker, stronger wall. However, the strength of a balloon wall, and more particularly the burst strength of the balloon wall, is a critical design parameter that may make reducing the balloon wall thickness impractical for lowering the force necessary to retract the balloon.

SUMMARY OF THE INVENTION

In at least one embodiment of the present invention, a balloon catheter for deployment within a body vessel is provided. The balloon catheter comprises a shaft having a lumen formed therethrough. Connected to the shaft is an inflatable balloon. The inflatable balloon has a balloon wall defining a balloon interior surface and a balloon exterior surface that is opposite the interior surface. In fluid communication with the balloon wall is the lumen for inflating the balloon to define an inflated state and for collapsing the balloon to define a deflated state. The balloon wall is textured in the deflated state such that the balloon interior surface is spatially registered with the balloon exterior surface. The balloon in the inflated state is tensioned to have a surface roughness substantially less than a surface roughness of the balloon in the deflated state.

In one aspect, the shaft has a proximal portion extending to a distal portion. The inflatable balloon is connected to the distal portion of the shaft. The texture of the balloon wall reduces force for collapsing the balloon to facilitate retrieval of the balloon catheter from the body vessel.

In at least one other embodiment of the present invention, a catheterization kit for use in the body vessel is provided. The kit includes an introducer sheath having a proximal section extending to a distal section and a sheath lumen formed therethrough. A balloon catheter as discussed in the foregoing paragraphs has an axial length disposed within the sheath lumen of the introducer sheath for relative axial movement therein. A wire guide is provided that includes a distal part disposed within the sheath lumen for relative axial movement therein. The distal part of the wire guide is for being positioned adjacent to a treatment location within the body vessel to guide the balloon to the treatment location for treating thereto in the inflated state. The texture of the balloon wall reduces force for collapsing the balloon to facilitate the retraction of the balloon into the sheath lumen for retrieval of the balloon catheter from the body vessel.

In at least one other embodiment of the present invention, a method for making a balloon catheter is provided. The method comprises blow molding a heated resin within a mold to produce a balloon. The mold has an internal mold surface that is textured to define a mold surface profile with a corresponding mold surface roughness value. Blow molding of the heated resin includes forming a heated resin wall that has an exterior resin surface facing the interior mold surface and an interior resin surface that is opposite the exterior resin surface. The heated resin wall is pressurized such that the exterior resin surface conforms to the texture of the internal mold surface and the interior resin surface is spatially registered with the exterior resin surface to define a heated resin wall texture. The heated resin wall is cooled to form a balloon wall having a balloon texture which corresponds to the heated resin wall texture to define the balloon. The balloon is attached to a shaft to form the balloon catheter. The balloon is in fluid communication with the shaft to be inflatable to tension the balloon, substantially reducing a surface roughness of the balloon.

Further objects, features, and advantages of the invention will become apparent from consideration of the following description and the appended claims when taken in connection with the accompanying drawings.

BRIEF DESCRIPTION OF THE DRAWINGS

FIG. 1 is a side view of one embodiment of a catheterization kit for use in a body vessel according to the present invention;

FIG. 2 is an exploded view of the catheterization kit depicted in FIG. 1 with a balloon catheter in an inflated state;

FIG. 3a is a sectional view of the distal tip of the catheter kit depicted in FIG. 1 along the line 3a-3a;

FIG. 3b is a sectional view of the shaft of the catheterization kit depicted in FIG. 1 along the line 3b-3b;

FIG. 5d is a random pattern texture in accordance with one embodiment of the present invention;

DETAILED DESCRIPTION

Figure 7:
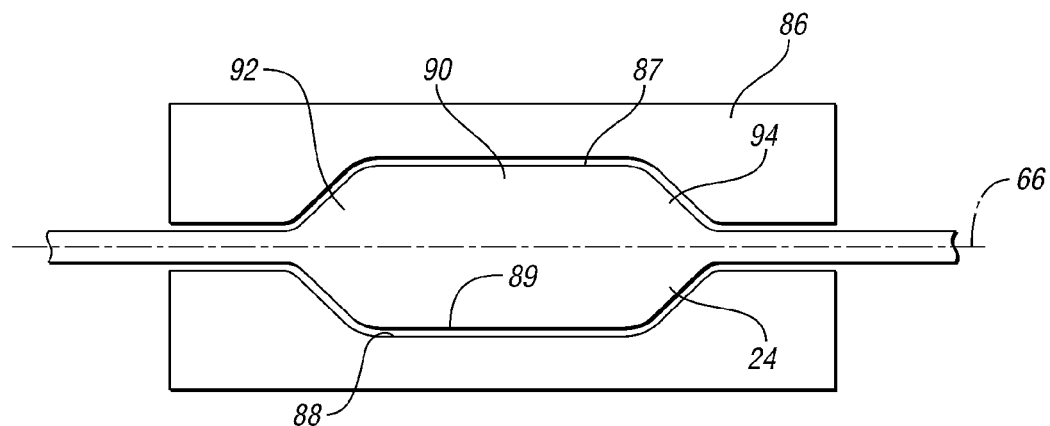
FIG. 7 is a sectional view of a balloon for the balloon catheter being blow molded in a mold in accordance with one embodiment of the present invention.

Detailed embodiments of the present invention are disclosed herein. It is understood however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis with the claims and for teaching one skilled in the art to practice the present invention.

Referring now to FIGS. 1-3b, a pushable balloon catheterization kit in accordance to one embodiment of the present invention is illustrated therein and designated at 10. The kit 10 includes a balloon catheter 12. The balloon catheter 12 comprises a shaft 14 having a proximal portion 16 extending to a distal portion 18. An inflatable balloon 24 is cooperable with the distal portion 18 of the shaft 14.

The shaft 14 and the inflatable balloon 24 may be made of any appropriate flexible material for use as a catheter. The material may include, for example, nylon, polyester, polytetrafluoroethylene (PTFE), latex, rubber, and mixtures thereof.

In one embodiment, the balloon 24 is made from a low or non-compliant material, such as for example, nylon or polyester. The compliant characteristics of the balloon 24 affect how the physician may use the balloon catheter 12. A low or non-compliant balloon will increase in diameter by up to a maximum of about 5% of its normal diameter in response to increasing the pressure for inflating the balloon 24 to between about 5 to 20 atmospheres. One example use for the low or non-compliant balloon 24 may be to dilate it for cracking lesions within a restricted portion of the body vessel while minimizing the likelihood of damaging an adjacent non-restricted portion of the body vessel. Alternatively, the balloon 24 may be made from a hybrid or highly compliant material where the diameter of the balloon may increase as much as about 40% during inflation. The hybrid or highly compliant balloon 24 may proportionally increase in diameter in response to increases in inflation pressure which may allow for fewer balloon sizes to be used to treat a wider range of vessel diameters.

The shaft 14 as illustrated in FIGS. 3a and 3b may include an outer lumen 20 and an inner lumen 22. The outer and inner lumens 20 and 22 extend from the proximal portion 16 towards the distal portion 18 and may be defined by first and second walls 21 and 23, respectively. In one example, the second wall 23 extends distally beyond the first wall 21. The inflatable balloon 24 is in fluid communication with the outer lumen 20 and the second wall 23 may extend at least to the distal end of the balloon 24 so that the inner lumen 22 is not in fluid communication with the balloon 24.

The balloon 24 has a balloon wall 26 comprising a balloon interior surface 28 and a balloon exterior surface 30 that is opposite the balloon interior surface 28. In one embodiment, the balloon 24 has a proximal balloon aperture 32 and a distal balloon aperture 34. The proximal and distal balloon apertures 32 and 34 are cooperable with the distal portion 18 of the shaft 18 and attach thereto at axial locations 36 and 38. As illustrated, the balloon 24 attaches to the first wall 21 of the shaft 14 at axial location 36 and to the second wall 23 of the shaft 14 at axial location 38. The balloon 24 may be attached to the shaft 14 by any suitable means, such as for example, hot melt bonding, adhesive bonding, solvent bonding or ultrasonic welding.

In this embodiment, at the proximal end 16 of the shaft 14 is an injection port 40 as depicted in FIGS. 1 and 2. The injection port 40 provides access for injecting a fluid to be advanced through the outer lumen 20 to the balloon 24 for inflating the balloon 24 to define an inflated state 42 (shown in phantom in FIG. 3a). The fluid may also be removed from the balloon 24 through the outer lumen 20 and the injection port 24 to collapse the balloon 24 to define a deflated state 44. In one example, the balloon 24 in the inflated state 42 has an internal pressure of at least about 5 atmospheres and the balloon 24 in the deflated state 44 has a pressure of less than about 5 atmospheres and preferably between about 0 and 1 atmosphere (0.0 to 14.7 psi or −14.7 to 0.0 psig).

As shown in FIGS. 1 and 3a, the wall 26 of the balloon 24 is textured 50 in the deflated state 44. In one example, the texture 50 of a balloon wall 26 in the deflated state 44 corresponds to a random grain pattern, several examples of which are illustrated in FIGS. 5a-5f. In another example, texture 50 of the balloon wall 26 in the deflated state 44 corresponds to a repeating grain pattern, several examples of which are illustrated in FIGS. 6a-6e.

The catheterization kit 10 is shown in FIGS. 1 and 2, for example, as part of a catheterization system for treatment of the body vessel in accordance with one embodiment of the present invention. The delivery system may include a PTFE introducer sheath 80 for percutaneously introducing the kit 10 into a body vessel. Of course, any other suitable material for the introducer sheath 80 may be used without falling beyond the scope or spirit of the present invention. The introducer sheath 80 may have any suitable size, such as for example, between about 3 French to 8 French. The introducer sheath 80 serves to allow the balloon catheter 12 to be percutaneously inserted into a desired location in the body vessel. The introducer sheath 80 receives and provides stability to the balloon catheter 12 at a desired location of the body vessel. For example, the introducer sheath 80 is held stationary within a common visceral artery, and adds stability to the balloon catheter 12 as it is advanced through the introducer sheath 80 to desired treatment location in the vasculature.

The kit 10 may also include a wire guide 82 configured to be percutaneously inserted within the vasculature to guide the balloon catheter 12 to the desired location. The wire guide 82 may be manipulated through a wire guide port 84 of the balloon catheter 12 where the inner lumen 22 is fed over the wire guide 82 to provide the balloon catheter 12 with a path to follow as it is advanced within the body vessel.

When the distal tip 64 of the balloon catheter 12 is at the desired location in the body vessel, the wire guide 82 may optionally be removed. The balloon 24 may then be inflated to the inflated state 42 for treating the body vessel. After treatment of the body vessel, the balloon 24 is retracted by collapsing the balloon 24 and retracting the balloon 24 into a lumen of the sheath 80 for retrieval of the balloon catheter 12 from the body vessel in the deflated state 44. As will be discussed in further detail below, the texture 50 of the balloon wall 26 in at least one embodiment reduces the force for collapsing the balloon 24 to facilitate retraction of the balloon 24 into the lumen of the sheath 80.

Figure 4:
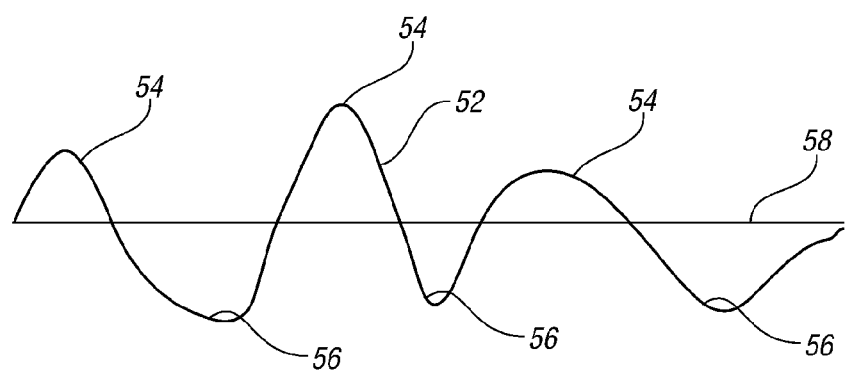
FIG. 4 is a diagram illustrating certain surface parameters.
Figure 5A:
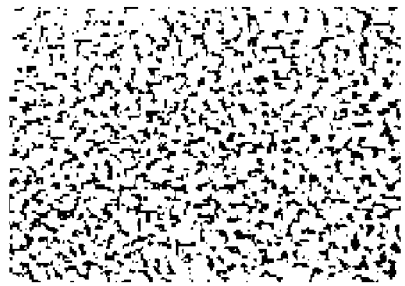
FIG. 5a is a random pattern texture in accordance with one embodiment of the present invention.
Figure 5B:
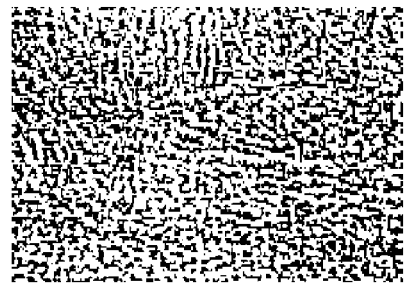
FIG. 5b is a random pattern texture in accordance with another embodiment of the present invention.
Figure 5B:
Figure 5C:
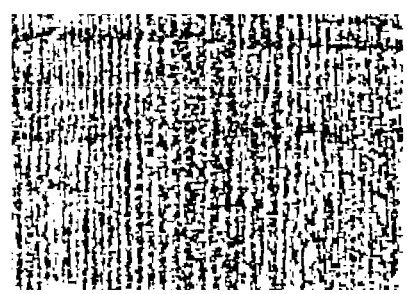
FIG. 5c is a random pattern texture in accordance with yet another embodiment of the present invention.
Figure 5E:
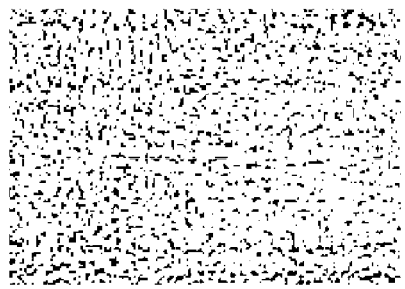
FIG. 5e is a random pattern texture in accordance with another embodiment of the present invention.
Figure 5F:
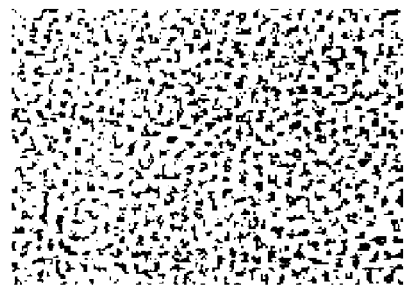
FIG. 5f is a random pattern texture in accordance with yet another embodiment of the present invention.
Figure 6A:
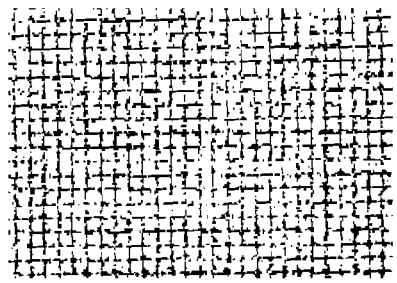
FIG. 6a is a repeating pattern texture in accordance with one embodiment of the present invention.
Figure 6B:
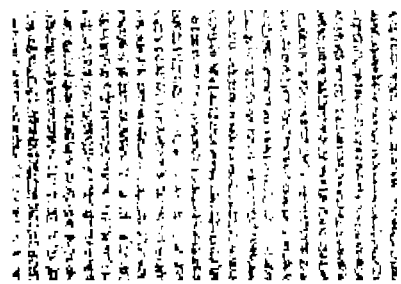
FIG. 6b is a repeating pattern texture in accordance with another embodiment of the present invention.
Figure 6C:
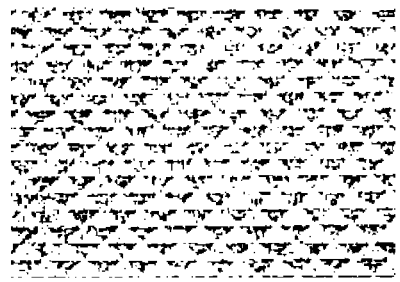
FIG. 6c is a repeating pattern texture in accordance with yet another embodiment of the present invention.
Figure 6D:
FIG. 6d is a repeating pattern texture in accordance with one embodiment of the present invention.
Figure 6E:
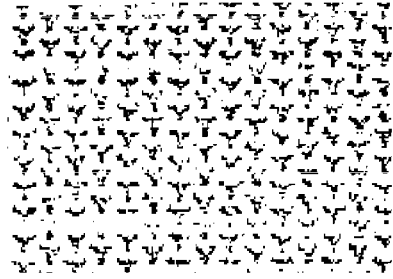
FIG. 6e is a repeating pattern texture in accordance with another embodiment of the present invention.

Referring to FIG. 4, further details regarding texture and surface roughness in accordance with at least one embodiment of the present invention are provided. A surface 52 may have a regular or irregular array of peaks 54 and valleys 56. A reference mean surface or surface centerline 58 is a datum surface that runs centrally through the peaks 54 and valleys 56 to divide the surface profile 52 so as to enclose equal areas above and below the surface centerline 58. Reference to the surface centerline 58 is used to measure the roughness of the surface 52. One particular type of surface roughness measurement is a numerical roughness average value ($S_a$) which is an arithmetic average of the absolute values of the deviations of the surface 52 from the surface centerline 58 as measured normal to the surface centerline 58 (Note—$R_a$ is a one-dimensional equivalent of $S_a$, e.g., when surface 52 is measured in one direction relative to a center line included in the surface centerline 58). The roughness average ($S_a$) may be expressed in microns (μm).

Figure 8A:
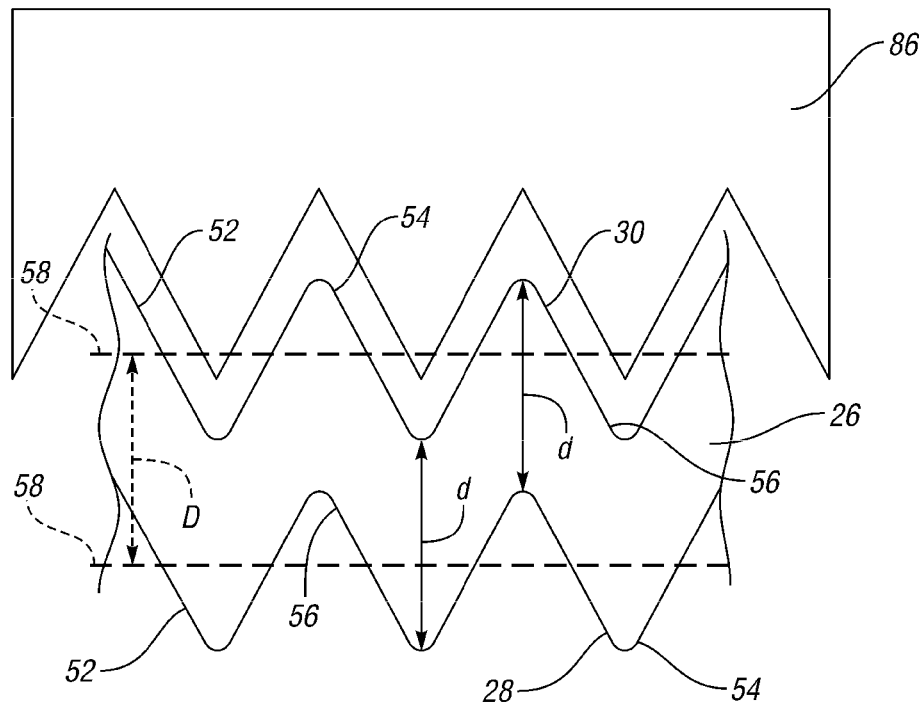
FIG. 8a is an enlarged sectional view of a balloon wall in a mold in accordance with an embodiment of the present invention.
Figure 8B:
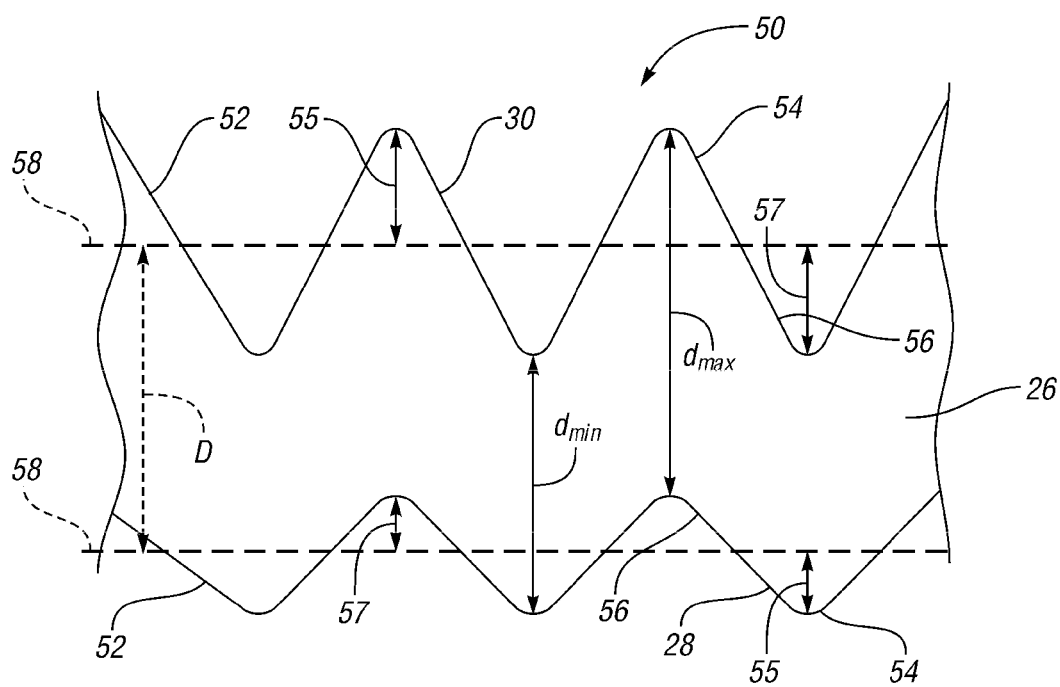
FIG. 8b is an enlarged sectional view of the balloon wall in accordance with one embodiment of the present invention.

Referring also to FIGS. 8a and 8b, the texture 50 of the balloon wall 26 is such that the balloon interior surface 28 is spatially registered with the balloon exterior surface 30 providing corresponding surface profiles 46 and 48 with substantially matching surface roughness values. Spatially registered is hereinafter understood to mean that the surfaces 28 and 30 are substantially matched on opposing sides of the wall 26. For example, the surfaces 28 and 30 are corrugated, micro-corrugated or substantially parallel such that when measures by a surface profiler, e.g. Micro Photonics Nanovea 3D Profilometer™, with the measured surface facing upward, peaks 54 on the exterior surface 30 are opposite valleys 56 on the interior surface 28 and valleys 56 on the exterior surface 30 are opposite peaks 54 on the interior surface 28. Moreover, "substantially matching" is hereinafter understood to mean matching to within at least 40%. For example and as illustrated in FIG. 8b, an interior surface 28 that substantially matches an exterior surface 30 will have valley depths 57 and peak heights 55 that correspond to at least 40% of the peak heights 55 and valley depths 57 of the exterior surface 30 (note—peak heights and valley depths are measure relative their corresponding surface centerline 58. Moreover, substantially matching surface roughness values for the interior and exterior surfaces 28 and 30 is hereinafter understood to mean that the magnitude of the surface roughness values of the interior surface 28 are at least 40% of the corresponding magnitude of the surface roughness values of the exterior surface 30 (using the absolute values for the surface roughness values to account for any opposing directional effects due to the spatially registered peaks and valleys).

In an example of the balloon 24 in the deflated state 44, the surface roughness value of the exterior surface 30 is at least an average roughness ($S_a$) of about 2 microns and preferably, is about 3 microns or more. Moreover, the surface roughness value of the balloon interior surface 28 is at least an average roughness ($S_a$) of about 1.5 microns. Preferably in this example, a ratio of the surface roughness value of the balloon exterior surface 30 to the surface roughness value of the balloon interior surface 28 does not exceed about 2:1.

In one example of the balloon in the inflated state 42, the balloon wall 26 is tensioned such that the texture 50 is substantially smoothed or nearly eliminated, thereby reducing the surface roughness of both the balloon interior and exterior surfaces 28 and 30 relative to the surfaces 28 and 30 in the deflated state 44. Applicants have found that by texturing the balloon wall 26 such that the texture 50 is prominent in the deflated state 44 but significantly diminishes in the inflated state 42 only to become prominent again when the balloon 24 is subsequently deflated, that the column strength of the balloon 24 may be significantly reduced without substantially decreasing the burst strength of the balloon 24. This modulating texture 50 of the balloon wall 26 preferably reduces the force for collapsing the balloon 24, facilitating retrieval of the balloon catheter 12 from the body vessel. The balloon 24 of the present invention may be configured at various nominal thicknesses D including nominal thicknesses in the range of about 0.0005 in to 0.0025 in, which provided suitable results in combination with the modulating texture 50 for reducing the column strength of the balloon 24 without substantially decreasing its burst strength.

In one embodiment, the surface roughness value of the exterior surface 30 of the balloon 24 in the inflated state 42 is reduced by at least about 50% from the surface roughness value of the exterior surface 30 in the deflated state 44. In another embodiment, the surface roughness value of the balloon interior surface 28 in the inflated state 42 is reduced by at least about 50% from the surface roughness value of the interior surface 28 in the deflated state 44.

Figure 9A:
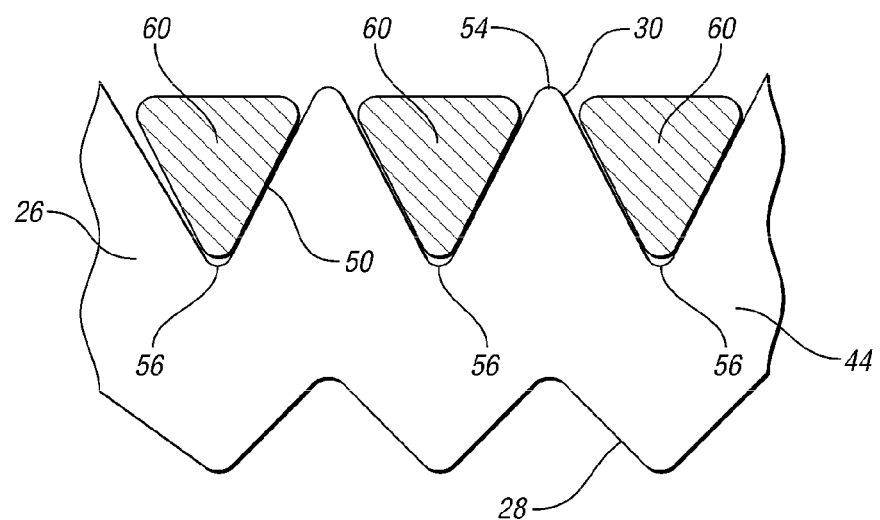
FIG. 9a is an enlarged sectional view of the balloon wall in a deflated state in accordance with an embodiment of the present invention.
Figure 9B:
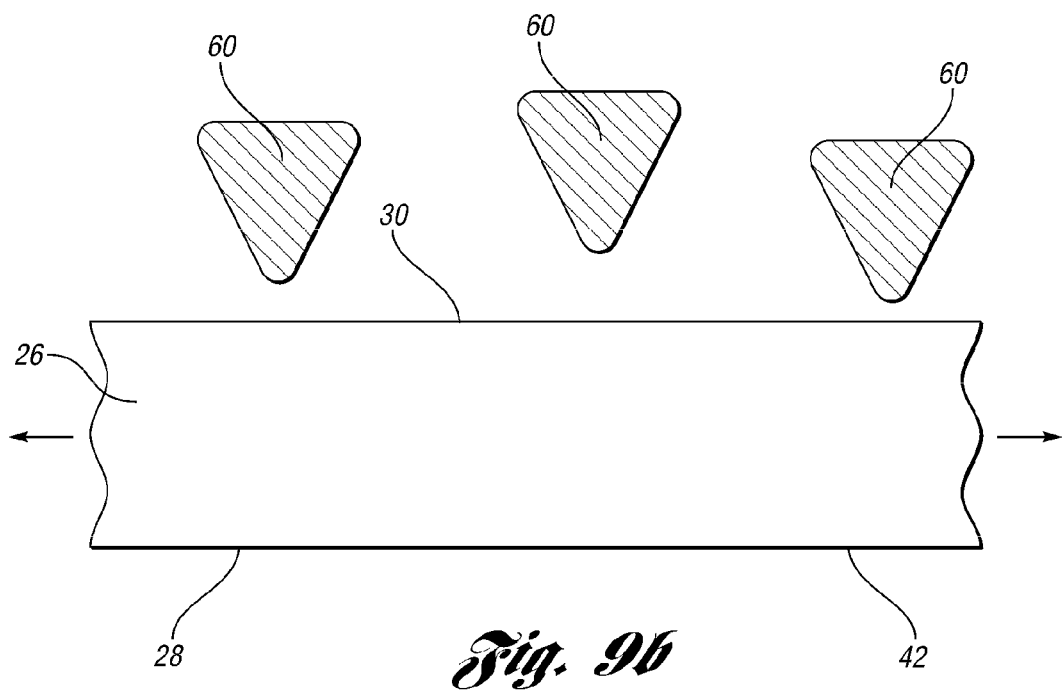
FIG. 9b is an enlarged sectional view of the balloon wall in an inflated state in accordance with an embodiment of the present invention.

Referring to FIGS. 9a and 9b, at least one other embodiment of the present invention is provided. The rough profile or texture 50 of the exterior balloon surface 30 in the deflated state 44 may be used to transfer medicants 60 to a treatment site in the body vessel. Specifically, the volume created between the valleys 56 and the peaks 54 in the surface 30 represent potential sites for the deposit of various bioactive materials which may be delivered to a stenosis or other body location. Medicants 60 such as Paclitaxel, Sirolimus, and Everolinus, or other commonly known medicants may be used to minimize restenosis of the body vessel. The medicants 60 can be coated onto the surface 30 of the balloon 24 while in the deflated state 44, filling in the texture 50. Upon inflation within the body vessel to the inflated state 42, the exterior balloon surface 30 is smoothed by the tensioning of the balloon wall 26 so that the valleys 56 and the peaks 54 diminish, thereby forcefully implanting the medicants 60 into the treatment area, e.g., stenosis, of the body vessel.

Figure 10A:
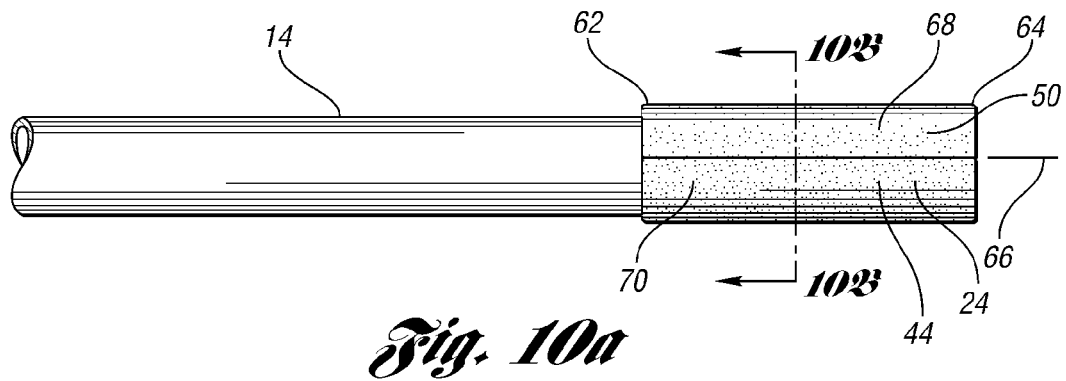
FIG. 10a is a side view of a deflated, folded balloon in accordance with one embodiment of the present invention.
Figure 10B:
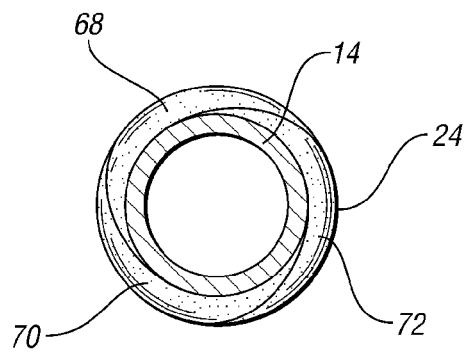
FIG. 10b is a sectional view of the deflated, folded balloon depicted in FIG. 10a along the line 10b-10b.

Referring to FIGS. 10a and 10b, at least one other embodiment of the present invention is provided. The balloon 24 has a proximal balloon end 62 and a distal balloon end 64 and a longitudinal axis 66 extending between the proximal and distal balloon ends 62 and 64. The balloon 24 may be folded in the deflated state 44 to provide a low profile configuration for being advanced into the body vessel for deployment therein. In one example, the balloon 24 is folded so as to form at least 3 folded portions 68, 70 and 72 extending between the proximal and distal balloon ends 62 and 64. The folded portions 68, 70 and 72 may be folded about the longitudinal axis 66 either clockwise or counter-clockwise. When the balloon 24 is deployed, the folded portions 68, 70 and 72 unfold about the longitudinal axis 66 thereby allowing the balloon 24 to expand to the inflated state 42.

Figure 11:
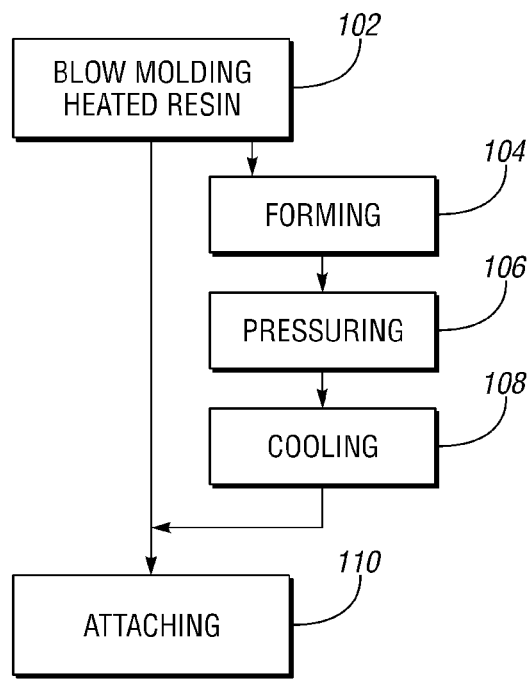
FIG. 11 is a flow-chart describing an example method for making the balloon catheter according to the present invention.

Referring to FIGS. 7, 8a and 11, a method for making a balloon catheter in accordance with at least one embodiment of the present invention is provided. The method comprises blow molding a heated resin at 102 within a mold 86 to produce a balloon 24. The resin may be heated via heaters or viscous dissipation, e.g., working of the resin through the molding process, or any other suitable means for heating the resin. The heated resin may be nylon or PET at a temperature at or above its respective glass transition T(g) or melting point T(m). Any other polymer suitable for blow molding may also be used.

The mold 86 has an internal mold surface 88 that is textured. The shape of the internal mold surface 88 correspond to the intended shape of the balloon 24 which is typically configured as a surface that has been rotated about its longitudinal axis 66. In one example, the balloon 24 has a shape that includes a cylindrical section 90, and proximal and distal frustoconical end sections 92 and 94.

As the mold is heated, air is blown into the tubular blank of heated resin to form a heated resin wall at 104 that may be shaped as a bubble having an exterior resin surface 87 facing the internal mold surface 88 and an opposed interior resin surface 89 positioned inside of the bubble. The heated resin is further pressurized at 106 by the air (sometimes referred to as packing-out) such that the exterior resin surface 87 conforms to the texture of the internal mold surface 88 and the interior resin surface 89 is spatially registered with the exterior resin surface 87 to define a heated resin wall texture. Notably, the temperature of the heated resin relative to its T(g) or T(m) and the amount of pressurizing affects the extent to which the exterior resin surface 87 conforms to the texture of the mold surface 88 and the extent to which the interior resin surface 89 becomes spatially registered with the exterior resin surface 87.

The heated resin wall is then cooled at 108 to form the balloon wall having a balloon texture which corresponds to the heated resin wall texture. The wall thickness of the finished balloon 24 is determined by the interaction of various factors, including the wall thickness of the heated resin blank, the external diameter of the finished balloon 24, the temperature and rate of change of temperature of the mold 86, the stretching and tensioning of the heated resin wall and the pressure and rate of change of pressure of the air blown into the heated resin blank.

The internal mold surface 88 is textured with a carefully selected grain pattern to provide a targeted surface roughness average value for the mold surface 88. The roughness of the mold surface 88 will typically be greater than the roughness of the finished balloon 24 (See FIG. 8a). In one example, a balloon 24 having an exterior surface 30 with a roughness average ($S_a$) of 3 microns is molded in a mold 86 having an internal mold surface 88 with a roughness average ($S_a$) of at least about 6 microns.

Applicant has also found that the method for graining the mold 86 may influence the effectiveness of the modulating texture 50 to reduce the column strength of the balloon 24 without substantially decreasing its burst strength. Specifically, both chemical etching and electrical discharge machining (EDM) where used to grain different mold surfaces 88. Chemically etching is a process where the mold surface 88 is selectively etched with an acid solution to provide a texture. Grain patterns using this method may have a more repeating pattern as illustrated in FIGS. 6a-6e. Alternatively, EDM or spark erosion moves an eroding electrode relative to the mold surface 88 to create a plurality of random arc formations therebetween to produce a texture on the surface 88. Grain patterns using this method may have a more random pattern as illustrated in FIGS. 5a-5f. Both processes result in a micron level texture being formed thereon. However, Applicant found that the balloons 24 that were textured with a more random grain pattern require less force for collapsing than balloons 24 that were textured with a more repeating pattern. The surface roughness values of the random and repeating grain patterns used were the same.

The method further comprises attaching at 110 the balloon 24 to the shaft 14 to form the balloon catheter 12. The balloon 24 may be attached at its proximal and distal ends 62 and 64 by being hot melted, adhesively bonded or solvent fused to the distal portion 18 of the shaft 14. Any other suitable means known to those skilled in the art may also be used to attach the balloon 24 to the shaft.

To further illustrate examples of the present invention, two series of tests will now be discussed. Provide below are tables 1a-1c that summarize a first series of tests which includes sheath compatibility testing and the force required for collapsing balloons which were molded in different surface finished molds. One mold had a polished surface (typically used for medical molding balloons), and the two other molds were finished with random surface patterns having surface roughness averages ($R_a$) of 6 μm and 12 μm respectively. The proximal and distal taper results correspond to the force required for collapsing the proximal and distal frustoconical sections 92 and 94 of the balloon 24 into the sheath 80. The test results indicate that the balloons molded in higher surface roughnesses molds required significantly less force for being collapsed into the sheath than balloons molded in lower surface roughnesses or smoothly polished molds. Specifically, balloons molded in the 12 $R_a$ mold required an average of 1.93 lbf to collapse the distal tapers, representing the highest force required for retrieval of the balloons, while balloons from the 6 $R_a$ mold and the smooth mold required an average of 2.18 lbf and 2.62 lbf, respectively, to collapse the distal tapers.

TABLE 1a

| Sheath Compatibility test | | | Smooth Polished Mold | | | |
|---|---|---|---|---|---|---|
| Sample Info | | Sheath | Quantitative Results (lbf) | | | |
| Sample # | Size | Lot # | Size Used (fr) | Proximal Taper | Distal Taper | Within Sheath | Comments |
| 1 | 8-4 | P1824790 | 6 | 1.65 | 3.00 | 1.35 | Average balloon dwall = .0805 mm |
| 2 | 8-4 | P1824790 | 6 | 2.65 | 2.45 | 1.50 | Average balloon dwall = .0805 mm |
| 3 | 8-4 | P1824790 | 6 | 1.70 | 2.40 | 1.50 | Average balloon dwall = .0805 mm |
| | | | Averages | 2.00 | 2.62 | 1.45 | |

TABLE 1b

| Sheath Compatibility test | | | 6 Ra mold (random EDM pattern) | | | |
|---|---|---|---|---|---|---|
| Sample Info | | Sheath | Quantitative Results (lbf) | | | |
| Sample # | Size | Lot # | Size Used (fr) | Proximal Taper | Distal Taper | Within Sheath | Comments |
| 1 | 8-4 | P1889196 | 6 | 1.30 | 2.45 | 1.55 | Average balloon dwall = .0795 mm |
| 2 | 8-4 | P1889196 | 6 | 1.65 | 2.15 | 1.35 | Average balloon dwall = .0795 mm |
| 3 | 8-4 | P1889196 | 6 | 1.20 | 1.95 | 1.15 | Average balloon dwall = .0795 mm |
| | | | Averages | 1.38 | 2.18 | 1.35 | |

TABLE 1c

| Sheath Compatibility test | | | 12 Ra mold (random EDM pattern) | | | |
|---|---|---|---|---|---|---|
| Sample Info | | Sheath | Quantitative Results (lbf) | | | |
| Sample # | Size | Lot # | Size Used (fr) | Proximal Taper | Distal Taper | Within Sheath | Comments |
| 1 | 8-4 | P1899197 | 6 | 1.05 | 2.00 | 1.25 | Average balloon dwall = .083 mm |
| 2 | 8-4 | P1899197 | 6 | 1.15 | 1.85 | 0.90 | Average balloon dwall = .083 mm |
| 3 | 8-4 | P1899197 | 6 | 0.85 | 1.95 | 0.95 | Average balloon dwall = .083 mm |
| | | | Averages | 1.02 | 1.93 | 1.03 | |

In a second series of tests summarized below in tables 2a-2b balloons with different surface roughness textures were evaluated. The balloons were measured using a variety of different surface roughness measurements when in the deflated and inflated states. A Micro Photonics Nanovea 3D Profilometer™ surface profiler unit was used to make the various measurements on the balloons. Group A and group B were textured balloons in the deflated state that were molded in molds having surface profiles with a surface roughness $R_a$ of 12 μm and 2 μm respectively. Group C and group D were textured balloons inflated to between about 1 atmosphere (14.7 psig) and 12 atmospheres (176.4 psig) gauge pressure as indicated and were molded in molds having surface profiles with a surface roughness $R_a$ of 12 μm and 2 μm respectively. The surface roughness measurement used to characterize the texture of these balloons were the Sq (root mean square height), Ssk (skewness), Sku (kurtosis), Sp (maximum peak height), Sv (maximum pit height or valley depth), Sz (maximum height), Sa (arithmetic mean height, Sdq (root mean square gradient), Sds (density of summits) and Spd (density of peaks).

The textured balloons molded in molds having a surface profile with a surface roughness of $R_a$ 12 μm (groups A and C) performed better than textured balloons molded in molds having a surface profile with a surface roughness of $R_a$ 2 μm (groups B and D). However, all of the textured balloons performed in accordance with the present invention and required less force for collapsing than balloons molded in convention molds with smooth surface profiles, e.g., balloons tested and reported in Table 1a.

It is believed that several of the different types of surface roughness measurements provided below facilitate identifying textures which perform in accordance with the present invention. For example, the $S_a$ values for the OD (outer surface) and the ID (internal surface) of the group A and B balloons are 4.74 and 4.43 μm, and 1.47 and 1.41 μm respectively. In both groups, the $S_a$ average in the deflated state of the ID nearly matches (within 90%) that of the OD.

In another example, the Ssk or skewness may be used to determine if the texture of the balloon in the deflated state is "spatially registered." Specifically, the Ssk describes the asymmetry of the height distribution histogram. That is, if the Ssk=0, then a symmetric height distribution is indicated, if the Ssk>0, then a higher peak distribution is indicated, e.g., flat surface with peaks, and if Ssk<0, then a higher valley distribution is indicated, e.g., flat surface with pits.

The Ssk of the OD and ID of the group A and B balloons are −0.631 and 0.613, and −0.28 and 0.235 respectively. This indicates that the OD's for both the group A and B balloons have higher valley distributions while their respective ID's have higher peak distributions. Notably, when the Ssk of the OD and the ID are combined within each group the sum is near zero, indicating that the peak and valley distributions of the opposing surfaces is practically matched (e.g. group A, the Ssk sum is −0.631+0.613=−0.018). This near zero value for the sum of the Ssk values of the opposed surfaces indicates that the surfaces are spatially registered.

In yet another example, the Sku or kurtosis may be used to describe the peakedness and randomness of the balloon's textured surface. Specifically, a Sku value of 3 indicates a perfect Gaussian random surface pattern. The further a value is from 3 (e.g., lower or higher than 3) the less random the surface pattern. Moreover, a high Sku value indicates a high proportion of the surface profile heights falling within a narrow range of heights, e.g., a compressed profile. Notably, the Sku values of the OD and ID of the group A and B balloons are 3.45 and 3.41, and 2.94 and 2.77 respectively. This indicates that the balloons of group A and group B have surface texturing patterns that are very random. Also, the Sku values for the group C and D balloons (only OD measurements were made on the groups C and D balloons) increased steadily when the balloons were inflated from 1 atmosphere gauge pressure to 8 or 12 atmospheres gauge pressure (e.g., Sku of 8.78 for group C balloons at 12 atm gauge pressure and Sku of 15 for group D balloons at 8 atm gauge pressure), indicating that the balloons were flattening or smoothing out, e.g., the respective textures modulated. In one embodiment, balloons in the deflated state are textured with a surface profile having Sku values between about 2.0 and 4.0.

In another example, the Sds or density of summits may be used to describe the number of local maximum peaks per area. The Sds is similar to the Spd or density of the peaks, but uses a more sensitive EUR 15178N testing standard. Specifically, the Sds considers a peak a maximum only if it is higher than its 8 neighboring peaks. This is a spatial parameter which is indicative of peak spacing. The larger the Sds values the further the maximum peaks are to one another. In one embodiment, Sds values between about 50 and 1000 are preferred for the textures of balloons in the deflated state. Notably, the Sds values for the OD and ID of the group A and B balloons are 180 and 102, and 449 and 574 respectively. Also, as the balloons are inflated, as in the group C and D balloons, the Sds values significantly increase, illustrating the modulating texture or smoothing of the balloons surfaces, e.g., Sds of 2948 per $mm^2$ for the group C balloons at 12 atm gauge pressure and 4001 per $mm^2$ for the group D balloons at 8 atm gauge pressure.

TABLE 2a

| Height Parameters | Raw Balloon Material Description | Unit | Group A, 12 Ra, 10 × 4 OD | ID | Group B, 2 Ra, 12 × 8 OD | ID | Smooth/Polished Mold, OD | ID |
|---|---|---|---|---|---|---|---|---|
| Sq | Root mean square height | μm | 5.95 | 5.66 | 1.82 | 1.75 | 0.237 | 0.176 |
| Ssk | Skewness | — | −0.631 | 0.613 | −0.28 | 0.235 | −0.238 | 0.553 |
| Sku | Kurtosis | — | 3.45 | 3.41 | 2.94 | 2.77 | 3.83 | 5.17 |
| Sp | Maximum peak height | μm | 13.4 | 20.5 | 5.35 | 5.62 | 2.09 | 2.36 |
| Sv | Maximum pit height | μm | 27.3 | 11.8 | 9.16 | 4.45 | 1.12 | 1.12 |
| Sz | Maximum height | μm | 40.7 | 32.3 | 14.5 | 10.1 | 3.21 | 3.48 |
| Sa | Arithmetic mean height | μm | 4.75 | 4.43 | 1.47 | 1.41 | 0.186 | 0.136 |
| Hybrid Parameters | | | | | | | | |
| Sdq | Root mean square gradient | — | 0.183 | 0.144 | 0.104 | 0.0583 | 0.0479 | 0.0455 |
| Sds Featured Parameters | Density of summits | 1/mm^2 | 180 | 102 | 449 | 574 | 5428 | 5981 |
| Spd | Density of peaks | 1/mm^2 | 14 | 28 | 29 | 36 | 601 | 606 |

TABLE 2b

| Finished Catheters Under Pressure (OD measurements only) | Description | Unit | Group C, 12 Ra, 8 × 4 1 atm | 8 atm | 12 atm |
|---|---|---|---|---|---|
| Height Parameters | | | | | |
| Sq | Root mean square height | μm | 3.75 | 0.624 | 0.293 |
| Ssk | Skewness | — | −0.669 | −1.28 | −1.7 |
| Sku | Kurtosis | — | 3.62 | 5.64 | 8.78 |
| Sp | Maximum peak height | μm | 13.1 | 1.2 | 0.861 |
| Sv | Maximum pit height | μm | 16.8 | 3.58 | 2.31 |

TABLE 2b-continued

| | Description | Unit | 30 | 4.79 | 3.17 |
|---|---|---|---|---|---|
| Sz | Maximum height | μm | 30 | 4.79 | 3.17 |
| Sa | Arithmetic mean height | μm | 2.96 | 0.473 | 0.215 |
| Hybrid Parameters | | | | | |
| Sdq | Root mean square gradient | — | 0.138 | 0.0293 | 0.0188 |
| Sds | Density of summits | 1/mm^2 | 295 | 1770 | 2948 |
| Featured Parameters | | | | | |
| Spd | Density of peaks | 1/mm^2 | 17 | 13 | 15 |

| | | | Group D, 2 Ra, 12 × 8 | | |
|---|---|---|---|---|---|
| | Description | Unit | 1 atm | 4 atm | 8 atm |
| Height Parameters | | | | | |
| Sq | Root mean square height | μm | 0.316 | 0.212 | 0.0914 |
| Ssk | Skewness | — | −1.22 | −1.69 | −2.35 |
| Sku | Kurtosis | — | 5.42 | 8.07 | 15 |
| Sp | Maximum peak height | μm | 0.655 | 0.47 | 0.407 |
| Sv | Maximum pit height | μm | 2.1 | 1.65 | 1.22 |
| Sz | Maximum height | μm | 2.76 | 2.12 | 1.63 |
| Sa | Arithmetic mean height | μm | 0.242 | 0.153 | 0.0612 |
| Hybrid Parameters | | | | | |
| Sdq | Root mean square gradient | — | 0.0234 | 0.0227 | 0.014 |
| Sds | Density of summits | 1/mm^2 | 2161 | 3707 | 4001 |
| Featured Parameters | | | | | |
| Spd | Density of peaks | 1/mm^2 | 28 | 63 | 44 |

As a person skilled in the art will readily appreciate, the above description is meant as an illustration of the implementation of the principles of this invention. This description is not intended to limit the scope or application of this invention in that the invention is susceptible to modification, variation, and change, without departing from the spirit of this invention, as defined in the following claims.

The invention claimed is:

1. A method of making a balloon catheter comprising:
blow molding a heated resin within a mold to produce a balloon, the mold having an internal mold surface textured to define a mold surface profile with a corresponding mold surface roughness value, the blow molding including:
forming a heated resin wall that has an exterior resin surface facing the internal mold surface and an interior resin surface opposite the exterior resin surface;
pressurizing the heated resin wall such that the exterior resin surface conforms to the texture of the internal mold surface and the interior resin surface is spatially registered with the exterior resin surface such that a height of a peak of the outer surface is within 40% of a height of a corresponding peak of the inner surface, defining a heated resin wall texture; and
cooling the heated resin wall to form a balloon wall having a roughened surface which corresponds to the heated resin wall texture, defining the balloon; and
attaching the balloon to a shaft to form the balloon catheter, the balloon in fluid communication with the shaft to be inflatable to tension the balloon, substantially reducing a surface roughness of the balloon.

2. The method according to claim 1 wherein the mold surface roughness value is at least a numerical average surface roughness value ($R_a$) of about 6 microns.

3. The method according to claim 1 wherein the texture of the internal mold surface corresponds to a random grain pattern formed by electrical discharge machining the mold.

4. The method according to claim 1 wherein the texture of the internal mold surface corresponds to a repeating grain pattern formed by chemically etching the mold.

* * * * *

UNITED STATES PATENT AND TRADEMARK OFFICE
CERTIFICATE OF CORRECTION

PATENT NO. : 9,861,797 B2
APPLICATION NO. : 14/721566
DATED : January 9, 2018
INVENTOR(S) : Burton et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 114 days.

Signed and Sealed this
First Day of May, 2018

Andrei Iancu
*Director of the United States Patent and Trademark Office*